US006593463B1

(12) United States Patent
Chen et al.

(10) Patent No.: US 6,593,463 B1
(45) Date of Patent: Jul. 15, 2003

(54) MODIFIED MSP-1 NUCLEIC ACID SEQUENCES AND METHODS FOR INCREASING MRNA LEVELS AND PROTEIN EXPRESSION IN CELL SYSTEMS

(75) Inventors: Li How Chen, Acton, MA (US); Harry Meade, Newton, MA (US)

(73) Assignee: Genzyme Transgenics Corporation, Framingham, MA (US)

( * ) Notice: Subject to any disclaimer, the term of this patent is extended or adjusted under 35 U.S.C. 154(b) by 0 days.

(21) Appl. No.: 09/175,684

(22) Filed: Oct. 20, 1998

Related U.S. Application Data

(60) Provisional application No. 60/085,649, filed on May 15, 1998, and provisional application No. 60/062,592, filed on Oct. 20, 1997.

(51) Int. Cl.[7] .......................... C07H 21/04; C12P 21/06; C12N 15/09; C12N 15/00
(52) U.S. Cl. ..................... 536/23.7; 435/69.1; 435/69.3; 435/320.1; 424/93.2; 424/185.1; 424/268.1; 424/272.1; 530/300; 530/350
(58) Field of Search .......................... 424/272.1, 185.1, 424/268.1, 93.2; 435/320.1, 69.1, 69.3; 530/300, 350; 536/23.1

(56) References Cited

U.S. PATENT DOCUMENTS

| 5,231,168 A | * | 7/1993 | Dziegiel et al. ............ 530/350 |
| 5,736,131 A | * | 4/1998 | Bosch et al. ................ 424/93.2 |
| 5,795,737 A | * | 8/1998 | Seed et al. .................. 445/69.1 |

FOREIGN PATENT DOCUMENTS

| AU | 1997 48649 B2 | 4/1998 |
| EP | 0 682 115 A | 11/1995 |
| WO | WO 91 08216 A | 6/1991 |
| WO | WO 94 28930 | 12/1994 |
| WO | WO 97/30159 | 8/1997 |
| WO | WO 97 31115 A | 8/1997 |
| WO | WO 98 14583 | 4/1998 |

OTHER PUBLICATIONS

Chattergoon et al, 1997, FASEB J., 11: 753–763.*
Ebert et al, 1991, Biotechnology, 9: 935–838.*
Holder et al, 1985, Nature, 317: 270–273.*
Jongwutiwes et al, 1993, Mol. Biochem. Parasitol., 59: 95–100.*
Ledley et al, 1991, Hum. Gene Ther., 2: 77–83.*
McDonnell et al, 1996, The New England J. Med., 334(1): 42–45.*
Orkin et al, 1995, Report and Recommendations of Panel to Assess NIH Investment in Gene Therapy Res.*
Pharmacia Catalogue, 1995, p. 277.*
Wang et al, 1989, J. Biol. Chem., 264(35): 21116–21121.*
Zinkernagel et al, 1993, Fundamental Immunology, 3rd edition, Raven Press.*
Akashi et al, 1994, Blood, 83(11): 3182–3187.*

Gordan et al.; Genetic Transformation Mouse Enbryos by Microinjection of purified DNA; (1980); *Proc. Natl. Acad. Sci.*; 77: pp. 7380–7384.

Gorden et al.; Integration and Stable Germ Line Transmission of Genes Injected into Mouse Pronuclei; (1981); *Science*; 214: pp. 1244–1246.

Brinster et al.; Factors Affecting the Efficiency of Intoducing Foreing DNA into Mice by Microinjecting Eggs; (1985); *Proc. Natl. Acad. Sci.*; 82: pp. 4438–4442.

Palmiter et al.; Transgenic Mice; (1985); *Cell*; 41: pp. 343–345.

Wall et al.; Development of Porcine Ova That Were Centrifuged to permit Visualizaton of Pronuclei and Nuclei[1]; (1985); *Biol. Reprod.*; 32: pp. 645–651.

Shaw et al.; A Conserved AU Sequence from the 3'Untranslated Region of GM–CSF mRNA Mediates Selective mRNA Degradation; (1986); *Cell*; 46: pp. 659–667.

Simons et al.; Gene Transfer into Sheep; (1988); *Bio/Technology*; 6: pp. 179–183.

Chang et al.; Generalized Immunological Recognition of the Major Merozoite Surface Antigen (gp195) of *Plasmodium falciparum*; (1989); *Proc. Natl. Acad. Sci.*; 86: pp. 6343–6347.

Vilotte et al.; Efficient Tissue–Specific Expression of Bovine α–lactalbumin in Transgenic Mice; (1989); *Eur. J. Biochem.*; 186: pp. 43–48.

Buhler et al.; Rabbit β–Casein Promotor Directs Secretion of Human Interleukin–2 into the Milk of Transgenic Rabbits; (1990); *Bio/Technology*; 8: pp. 140–143.

Ebert et al.; Transgenic Production of A Variant of Human Tissue–Type Plasminogen Activator in Goat Milk Generation of Transgenic Goats . . . ; (1991);*Bio/Technology*; 9: pp. 835–838.

Krimenfort et al.; Generation of Transgenic Dairy Cattle Using 'In Vitro' Embryo Production; (1991) *Bio/Technology*; 9: pp. 844–847.

Wright et al.; High Level Expression of Active Human Alpha–1–Antitrypsin in the Milk of Transgenic Sheep; (1991); *Bio/Technology*; 9: 830–834.

(List continued on next page.)

Primary Examiner—Scott D. Priebe
Assistant Examiner—Peter Paras, Jr.
(74) Attorney, Agent, or Firm—Fish & Richardson P.C.

(57) ABSTRACT

The invention provides modified recombinant nucleic acid sequences (preferably DNA) and methods for increasing the mRNA levels and protein expression of malarial surface protein MSP-1 which is known to be difficult to express in cell culture systems, mammalian cell culture systems, or in transgenic animals. The preferred protein candidates for expression using the recombinant techniques of the invention are MSP-1 proteins expressed from DNA coding sequences comprising reduced overall AT content or AT rich regions and/or mRNA instability motifs and/or rare codons relative to the native MSP-1 gene.

22 Claims, 10 Drawing Sheets

OTHER PUBLICATIONS

Chang et al.; A Carboxyl–Terminal Fragment of *Plasmodium falciparum* gp195 Expressed by a Recombinant Baculovirus Induces Antibodies that . . . ; (1992); *J. Immunol*; 149: pp. 548–555.

Soulier et al.; Expression Analysis of Ruminant α–Lactalbumin in Transgenic Mice: Developmental Regulation and General Location of Important Cis–Regulatory . . . ; (1992); *FEBS Letters*: 297(1–2): pp. 13–18.

Wall et al.; Making Transgenic Livestock: Genetic Engineering on a Large Scale: (1992); *J. Cell. Biochem.*; 49: pp. 113–120.

Diggs et al.; The Major Merozoite Surface Protein as a Malaria Vaccine Target; (1993); Parasitology Today; 9(8): pp. 300–302.

Campbell et al.; Sheep Coloned by Nuclear Transfer from a Cultured Cell Line; (1996); *Nature*; 380: pp. 64–66.

Chang et al.; A Recombinant Baculovirus 42–Kilodalton C–Terminal Fragment of *Plasmodium falciparum* Merozoite Surface Protein 1 Protects Aotus Monkeys . . . ; (1996); *Infecton& Immunity*; 64(1): pp. 253–262.

Hochi et al.; Secretion of Bovine α–Lactalbumin Into the Milk of Transgenic Rats, (1992) *Molecular Reproduction and Development* 33: 160–164.

* cited by examiner

```
   1 gcCgtCactccCtccgtCatCgataacatCctGtcCaaGatCgaGaaCgaGtaCg
   1▶ AlaValThrProSerValIleAspAsnIleLeuSerLysIleGluAsnGluTyrG
  56 AGGTGCTGTACCTGAAGccGCTGGcaggGgtCtaCCgGagCCTGAAGAAGcaG
  19▶ luValLeuTyrLeuLysProLeuAlaGlyValTyrArgSerLeuLysLysGln
 109 CtGGaGaaCaacgtGatgacCttCaaCgtGaaCgtGaaggatatCCTGAACAGC
  37▶ LeuGluAsnAsnValMetThrPheAsnValAsnValLysAspIleLeuAsnSer
 163 cgGttCaaCaaGcgGGaGaaCttcaaGaaCgtGCTGGaGAGCgatCtGatCcc
  55▶ ArgPheAsnLysArgGluAsnPheLysAsnValLeuGluSerAspLeuIlePr
 216 CtaCaaGGatCtGacCAGCAGCaaCtaCgtGgtcaaGGatccCtaCaaGttCC
  72▶ oTyrLysAspLeuThrSerSerAsnTyrValValLysAspProTyrLysPheL
 269 tGaaCaaGGaGaaGaGaGataaGttcCtGagcagttaCaaCtaCatCaaggatAG
  90▶ euAsnLysGluLysArgAspLysPheLeuSerSerTyrAsnTyrIleLysAspSe
 324 CatTGatacCGatatCaaCttCgcCaaCgatGtCctGGgataCtaCaaGatCCt
 108▶ rIleAspThrAspIleAsnPheAlaAsnAspValLeuGlyTyrTyrLysIleLe
 378 GtccGaGaaGtaCaaGAGCgatCtGGatTCAatCaaGaaGtaCatcaacgaTaa
 126▶ uSerGluLysTyrLysSerAspLeuAspSerIleLysLysTyrIleAsnAspLy
 432 GcaGGGAGaGaaCGaGaaGtacCtGcccttCCTGaacaaCatCGagaccCtGta
 144▶ sGlnGlyGluAsnGluLysTyrLeuProPheLeuAsnAsnIleGluThrLeuTy
 486 CaaGacCgtCaaCgataaGattGatCtGttCgtGatCcaCCTGGaGGcCaaGGt
 162▶ rLysThrValAsnAspLysIleAspLeuPheValIleHisLeuGluAlaLysVa
                                                      NdeI
 540 CctGaaCtaCacatatgagaaGAGCaacgtGGaGGtCaaGatCaaGGaGctGaa
 180▶ lLeuAsnTyrThrTyrGluLysSerAsnValGluValLysIleLysGluLeuAs
 594 ttacCtGaaGacCatCcaGGaTaaGCTGGcCGattTCaaGaaGaaCaacaaCtt
 198▶ nTyrLeuLysThrIleGlnAspLysLeuAlaAspPheLysLysAsnAsnAsnPh
 648 cgtCGGGatCGcCGatCtGAGCacCGattaCaaccaCaaCaacCtGCTGacCaa
 216▶ eValGlyIleAlaAspLeuSerThrAspTyrAsnHisAsnAsnLeuLeuThrLy
 702 GttCCtGaGCacCGGtatGGtCttCGaaaaCctGGcCaaGaccGtCCTGAGCaa
 234▶ sPheLeuSerThrGlyMetValPheGluAsnLeuAlaLysThrValLeuSerAs
 756 CCTGCTGGatGGGaacCtGcaGGGGatGCtGaacatCAGCcaGcaccaGtGTgt
 252▶ nLeuLeuAspGlyAsnLeuGlnGlyMetLeuAsnIleSerGlnHisGlnCysVa
 810 GaaGaaGcaGtGtccCcaGaaCAGCgGGtgtttcagacaCCTGGatGaGaGa
 270▶ lLysLysGlnCysProGlnAsnSerGlyCysPheArgHisLeuAspGluArgGl
 864 GGaGtGtaaGtGtCtGCTGaaCtacaaGcaGGaaggtGataaGtGtGtGGaaaaC
 288▶ uGluCysLysCysLeuLeuAsnTyrLysGlnGluGlyAspLysCysValGluAsn
 919 ccCaatcctacttGtaacgaGaaCaatGGtGGatGtGatGCCGatGccaaGtGtaccG
 307▶ ProAsnProThrCysAsnGluAsnAsnGlyGlyCysAspAlaAspAlaLysCysThrG
 977 aGGaGGattcaggGagcaacGGGaaGaaGatcacCtGtGaGtGtacCaaGCctGatt
 326▶ luGluAspSerGlySerAsnGlyLysLysIleThrCysGluCysThrLysProAspS
1034 cttatccactGttcgatGGtatCttctGTagt
 345▶ erTyrProLeuPheAspGlyIlePheCysSer
```

FIG. 1

```
  1 GCAGTAACTCCTTCCGTAATTGATAACATACTTTCTAAAATTGAAAATGAATA
  1▶AlaValThrProSerValIleAspAsnIleLeuSerLysIleGluAsnGluTyrG
                              EcoNI (73)
 56 AGGTTTTATATTTAAAACCTTTAGCAGGTGTTTATAGAAGTTTAAAAAAACAATT
 19▶luValLeuTyrLeuLysProLeuAlaGlyValTyrArgSerLeuLysLysGlnLe
111 AGAAAATAACGTTATGACATTTAATGTTAATGTTAAGGATATTTAAATTCACGA
 37▶uGluAsnAsnValMetThrPheAsnValAsnValLysAspIleLeuAsnSerArg
166 TTTAATAAACGTGAAAATTTCAAAAATGTTTTAGAATCAGATTTAATTCCATATA
 56▶PheAsnLysArgGluAsnPheLysAsnValLeuGluSerAspLeuIleProTyrL
221 AAGATTTAACATCAAGTAATTATGTTGTCAAAGATCCATATAAATTTCTTAATAA
 74▶ysAspLeuThrSerSerAsnTyrValValLysAspProTyrLysPheLeuAsnLy
276 AGAAAAAAGAGATAAATTCTTAAGCAGTTATAATTATATTAAGGATTCAATAGAT
 92▶sGluLysArgAspLysPheLeuSerSerTyrAsnTyrIleLysAspSerIleAsp
331 ACGGATATAAATTTTGCAAATGATGTTCTTGGATATTATAAAATATTATCCGAAA
111▶ThrAspIleAsnPheAlaAsnAspValLeuGlyTyrTyrLysIleLeuSerGluL
386 AATATAAATCAGATTTAGATTCAATTAAAAAATATATCAACGACAAACAAGGTGA
129▶ysTyrLysSerAspLeuAspSerIleLysLysTyrIleAsnAspLysGlnGlyGl
441 AAATGAGAAATACCTTCCCTTTTTAAACAATATTGAGACCTTATATAAAACAGTT
147▶uAsnGluLysTyrLeuProPheLeuAsnAsnIleGluThrLeuTyrLysThrVal
496 AATGATAAAATTGATTTATTTGTAATTCATTTAGAAGCAAAAGTTCTAAATTATA
166▶AsnAspLysIleAspLeuPheValIleHisLeuGluAlaLysValLeuAsnTyrT
551 CATATGAGAAATCAAACGTAGAAGTTAAAATAAAAGAACTTAATTACTTAAAAAC
184▶hrTyrGluLysSerAsnValGluValLysIleLysGluLeuAsnTyrLeuLysTh
606 AATTCAAGACAAATTGGCAGATTTTAAAAAAAATAACAATTTCGTTGGAATTGCT
202▶rIleGlnAspLysLeuAlaAspPheLysLysAsnAsnAsnPheValGlyIleAla
661 GATTTATCAACAGATTATAACCATAATAACTTATTGACAAAGTTCCTTAGTACAG
221▶AspLeuSerThrAspTyrAsnHisAsnAsnLeuLeuThrLysPheLeuSerThrG
716 GTATGGTTTTTGAAAATCTTGCTAAAACCGTTTTATCTAATTTACTTGATGGAAA
239▶lyMetValPheGluAsnLeuAlaLysThrValLeuSerAsnLeuLeuAspGlyAs
771 CTTGCAAGGTATGTTAAACATTTCACAACACCAATGCGTAAAAAAACAATGTCCA
257▶nLeuGlnGlyMetLeuAsnIleSerGlnHisGlnCysValLysLysGlnCysPro
826 CAAAATTCTGGATGTTTCAGACATTTAGATGAAAGAGAAGAATGTAAATGTTTAT
276▶GlnAsnSerGlyCysPheArgHisLeuAspGluArgGluGluCysLysCysLeuL
881 TAAATTACAAACAAGAAGGTGATAAATGTGTTGAAAATCCAAATCCTACTTGTAA
294▶euAsnTyrLysGlnGluGlyAspLysCysValGluAsnProAsnProThrCysAs
936 CGAAAATAATGGTGGATGTGATGCAGATGCCAAATGTACCGAAGAAGATTCAGGT
312▶nGluAsnAsnGlyGlyCysAspAlaAspAlaLysCysThrGluGluAspSerGly
991 AGCAACGGAAAGAAAATCACATGTGAATGTACTAAACCTGATTCTTATCCACTTT
331▶SerAsnGlyLysLysIleThrCysGluCysThrLysProAspSerTyrProLeuP
                              PstI (1059)
1046 TCGATGGTATTTTCTGCAGTCACCACCACCACCACCACTAACT
349▶heAspGlyIlePheCysSerHisHisHisHisHisHis•••          FIG. 2
```

| Codon | AA | goat b-casein | goat K-casein | MSP wt | Edited MSP | mouse b-casein | mouse a-casein | mouse g-casein | mouse e-casein |
|---|---|---|---|---|---|---|---|---|---|
| TTT | Phe | 5 | 4 | 8 | 0 | 4 | 8 | 3 | 4 |
| TTC | Phe | 4 | 3 | 7 | 15 | 4 | 6 | 7 | 1 |
| TTA | Leu | 0 | 2 | 25 | 0 | 0 | 0 | 0 | 0 |
| TTG | Leu | 0 | 2 | 3 | 0 | 0 | 0 | 0 | 1 |
| TCT | Ser | 5 | 1 | 4 | 1 | 13 | 5 | 7 | 5 |
| TCC | Ser | 2 | 2 | 2 | 3 | 6 | 14 | 8 | 2 |
| TCA | Ser | 1 | 4 | 10 | 1 | 1 | 3 | 2 | 0 |
| TCG | Ser | 0 | 1 | 0 | 0 | 0 | 0 | 0 | 0 |
| TAT | Tyr | 2 | 7 | 17 | 2 | 1 | 3 | 2 | 1 |
| TAC | Tyr | 1 | 2 | 3 | 18 | 2 | 6 | 6 | 7 |
| TAA | *** | 1 | 2 | 0 | 0 | 1 | 0 | 1 | 0 |
| TAG | *** | 0 | 0 | 0 | 0 | 0 | 0 | 0 | 0 |
| TGT | Cys | 1 | 1 | 10 | 12 | 0 | 0 | 1 | 0 |
| TGC | Cys | 0 | 2 | 2 | 0 | 2 | 2 | 2 | 1 |
| TGA | *** | 0 | 0 | 0 | 0 | 0 | 1 | 0 | 1 |
| TGG | Trp | 1 | 1 | 0 | 0 | 0 | 2 | 2 | 2 |
| CTT | Leu | 9 | 1 | 9 | 0 | 16 | 9 | 3 | 3 |
| CTC | Leu | 5 | 2 | 0 | 0 | 7 | 8 | 0 | 1 |
| CTA | Leu | 1 | 2 | 1 | 0 | 1 | 2 | 1 | 0 |
| CTG | Leu | 11 | 5 | 0 | 38 | 10 | 17 | 4 | 1 |
| CCT | Pro | 17 | 6 | 4 | 2 | 8 | 6 | 3 | 0 |
| CCC | Pro | 12 | 0 | 1 | 6 | 8 | 6 | 6 | 4 |
| CCA | Pro | 3 | 13 | 5 | 1 | 5 | 6 | 2 | 2 |
| CCG | Pro | 1 | 1 | 0 | 1 | 0 | 0 | 0 | 1 |
| CAT | His | 0 | 1 | 3 | 0 | 2 | 6 | 2 | 1 |
| CAC | His | 5 | 3 | 1 | 4 | 4 | 0 | 3 | 0 |
| CAA | Gln | 5 | 9 | 9 | 0 | 9 | 21 | 9 | 7 |
| CAG | Gln | 16 | 6 | 0 | 9 | 21 | 32 | 12 | 8 |
| CGT | Arg | 0 | 1 | 1 | 0 | 0 | 0 | 0 | 0 |
| CGC | Arg | 0 | 0 | 0 | 0 | 1 | 0 | 0 | 0 |
| CGA | Arg | 0 | 0 | 1 | 0 | 0 | 0 | 0 | 1 |
| CGG | Arg | 1 | 0 | 0 | 3 | 0 | 0 | 0 | 0 |
| ATT | Ile | 4 | 5 | 13 | 0 | 3 | 4 | 3 | 4 |
| ATC | Ile | 6 | 3 | 2 | 20 | 7 | 5 | 8 | 5 |
| ATA | Ile | 1 | 3 | 5 | 0 | 1 | 0 | 2 | 0 |
| ATG | Met | 7 | 3 | 3 | 3 | 4 | 12 | 2 | 13 |
| ACT | Thr | 7 | 6 | 3 | 2 | 6 | 5 | 1 | 4 |
| ACC | Thr | 2 | 7 | 3 | 13 | 4 | 4 | 4 | 4 |
| ACA | Thr | 2 | 4 | 9 | 1 | 1 | 1 | 2 | 0 |
| ACG | Thr | 0 | 0 | 1 | 0 | 0 | 0 | 2 | 0 |
| AAT | Asn | 2 | 6 | 29 | 3 | 4 | 6 | 3 | 1 |
| AAC | Asn | 2 | 3 | 12 | 38 | 4 | 9 | 4 | 6 |
| AAA | Lys | 7 | 6 | 38 | 0 | 6 | 7 | 3 | 5 |
| AAG | Lys | 6 | 4 | 4 | 42 | 3 | 6 | 13 | 7 |
| AGT | Ser | 2 | 6 | 5 | 2 | 3 | 6 | 6 | 5 |
| AGC | Ser | 5 | 0 | 2 | 16 | 2 | 6 | 6 | 3 |
| AGA | Arg | 2 | 2 | 4 | 3 | 1 | 8 | 1 | 1 |
| AGG | Arg | 0 | 2 | 0 | 0 | 0 | 0 | 0 | 1 |
| GTT | Val | 5 | 6 | 15 | 0 | 7 | 4 | 2 | 3 |
| GTC | Val | 8 | 2 | 1 | 11 | 7 | 3 | 3 | 0 |
| GTA | Val | 2 | 2 | 5 | 0 | 2 | 4 | 1 | 3 |
| GTG | Val | 8 | 4 | 0 | 10 | 6 | 3 | 5 | 3 |
| GCT | Ala | 1 | 3 | 2 | 0 | 8 | 17 | 4 | 2 |
| GCC | Ala | 4 | 7 | 1 | 8 | 6 | 3 | 3 | 3 |
| GCA | Ala | 3 | 7 | 6 | 1 | 4 | 13 | 1 | 1 |
| GCG | Ala | 0 | 1 | 0 | 0 | 0 | 0 | 0 | 0 |
| GAT | Asp | 4 | 5 | 25 | 27 | 3 | 6 | 4 | 2 |
| GAC | Asp | 0 | 2 | 2 | 0 | 1 | 2 | 1 | 3 |
| GAA | Glu | 10 | 6 | 21 | 3 | 6 | 12 | 9 | 6 |
| GAG | Glu | 9 | 5 | 4 | 22 | 5 | 5 | 5 | 5 |
| GGT | Gly | 2 | 1 | 8 | 4 | 0 | 0 | 0 | 0 |
| GGC | Gly | 0 | 0 | 0 | 0 | 0 | 0 | 0 | 0 |
| GGA | Gly | 2 | 1 | 6 | 3 | 1 | 0 | 1 | 0 |
| GGG | Gly | 1 | 0 | 0 | 7 | 1 | 0 | 0 | 0 |

FIG. 3A

| Codon | AA | MSP wt | Edited MSP | MSP wt | Edited MSP | E.coli | Human |
|---|---|---|---|---|---|---|---|
| TTT | Phe | 8 | 0 | 0.53 | 0 | 0.5 | 0.35 |
| TTC | Phe | 7 | 15 | 0.47 | 1 | 0.5 | 0.65 |
| TTA | Leu | 25 | 0 | 0.66 | 0 | 0.11 | 0.05 |
| TTG | Leu | 3 | 0 | 0.08 | 0 | 0.11 | 0.09 |
| TCT | Ser | 4 | 1 | 0.17 | 0.04 | 0.27 | 0.17 |
| TCC | Ser | 2 | 3 | 0.09 | 0.13 | 0.21 | 0.26 |
| TCA | Ser | 10 | 1 | 0.43 | 0.04 | 0.13 | 0.11 |
| TCG | Ser | 0 | 0 | 0 | 0 | 0.14 | 0.07 |
| TAT | Tyr | 17 | 2 | 0.85 | 0.1 | 0.54 | 0.47 |
| TAC | Tyr | 3 | 18 | 0.15 | 0.9 | 0.46 | 0.53 |
| TAA | *** | 0 | 0 | | | | |
| TAG | *** | 0 | 0 | | | | |
| TGT | Cys | 10 | 12 | 0.83 | 1 | 0.45 | 0.3 |
| TGC | Cys | 2 | 0 | 0.17 | 0 | 0.55 | 0.7 |
| TGA | *** | 0 | 0 | | | | |
| TGG | Trp | 0 | 0 | 0 | 0 | 1 | 1 |
| CTT | Leu | 9 | 0 | 0.24 | 0 | 0.12 | 0.11 |
| CTC | Leu | 0 | 0 | 0 | 0 | 0.12 | 0.22 |
| CTA | Leu | 1 | 0 | 0.02 | 0 | 0.03 | 0.07 |
| CTG | Leu | 0 | 38 | 0 | 1 | 0.72 | 0.46 |
| CCT | Pro | 4 | 2 | 0.4 | 0.2 | 0.14 | 0.24 |
| CCC | Pro | 1 | 6 | 0.1 | 0.6 | 0.11 | 0.41 |
| CCA | Pro | 5 | 1 | 0.5 | 0.1 | 0.2 | 0.24 |
| CCG | Pro | 0 | 1 | 0 | 0.1 | 0.54 | 0.11 |
| CAT | His | 3 | 0 | 0.75 | 0 | 0.64 | 0.42 |
| CAC | His | 1 | 4 | 0.25 | 1 | 0.36 | 0.58 |
| CAA | Gln | 9 | 0 | 1 | 0 | 0.31 | 0.26 |
| CAG | Gln | 0 | 9 | 0 | 1 | 0.69 | 0.74 |
| CGT | Arg | 1 | 0 | 0.17 | 0 | 0.46 | 0.09 |
| CGC | Arg | 0 | 0 | 0 | 0 | 0.32 | 0.19 |
| CGA | Arg | 1 | 0 | 0.17 | 0 | 0.05 | 0.1 |
| CGG | Arg | 0 | 3 | 0 | 0.5 | 0.06 | 0.15 |
| ATT | Ile | 13 | 0 | 0.65 | 0 | 0.39 | 0.23 |
| ATC | Ile | 2 | 20 | 0.1 | 1 | 0.52 | 0.64 |
| ATA | Ile | 5 | 0 | 0.25 | 0 | 0.08 | 0.13 |
| ATG | Met | 3 | 3 | 1 | 1 | 1 | 1 |
| ACT | Thr | 3 | 2 | 0.19 | 0.13 | 0.36 | 0.2 |
| ACC | Thr | 3 | 13 | 0.19 | 0.81 | 0.38 | 0.47 |
| ACA | Thr | 9 | 1 | 0.56 | 0.06 | 0.09 | 0.21 |
| ACG | Thr | 1 | 0 | 0.06 | 0 | 0.17 | 0.12 |
| AAT | Asn | 29 | 3 | 0.71 | 0.07 | 0.29 | 0.34 |
| AAC | Asn | 12 | 38 | 0.29 | 0.93 | 0.71 | 0.66 |
| AAA | Lys | 38 | 0 | 0.9 | 0 | 0.72 | 0.45 |
| AAG | Lys | 4 | 42 | 0.1 | 1 | 0.28 | 0.55 |
| AGT | Ser | 5 | 2 | 0.21 | 0.09 | 0.11 | 0.11 |
| AGC | Ser | 2 | 16 | 0.09 | 0.7 | 0.14 | 0.29 |
| AGA | Arg | 4 | 3 | 0.67 | 0.5 | 0.08 | 0.24 |
| AGG | Arg | 0 | 0 | 0 | 0 | 0.03 | 0.23 |
| GTT | Val | 15 | 0 | 0.71 | 0 | 0.37 | 0.13 |
| GTC | Val | 1 | 11 | 0.05 | 0.52 | 0.12 | 0.27 |
| GTA | Val | 5 | 0 | 0.24 | 0 | 0.28 | 0.09 |
| GTG | Val | 0 | 10 | 0 | 0.48 | 0.23 | 0.5 |
| GCT | Ala | 2 | 0 | 0.22 | 0 | 0.33 | 0.31 |
| GCC | Ala | 1 | 8 | 0.11 | 0.89 | 0.18 | 0.4 |
| GCA | Ala | 6 | 1 | 0.67 | 0.11 | 0.28 | 0.17 |
| GCG | Ala | 0 | 0 | 0 | 0 | 0.21 | 0.12 |
| GAT | Asp | 25 | 27 | 0.93 | 1 | 0.48 | 0.38 |
| GAC | Asp | 2 | 0 | 0.07 | 0 | 0.52 | 0.62 |
| GAA | Glu | 21 | 3 | 0.84 | 0.12 | 0.67 | 0.4 |
| GAG | Glu | 4 | 22 | 0.16 | 0.88 | 0.33 | 0.6 |
| GGT | Gly | 8 | 4 | 0.57 | 0.29 | 0.46 | 0.15 |
| GGC | Gly | 0 | 0 | 0 | 0 | 0.4 | 0.44 |
| GGA | Gly | 6 | 3 | 0.43 | 0.21 | 0.06 | 0.17 |
| GGG | Gly | 0 | 7 | 0 | 0.5 | 0.08 | 0.24 |

Oligos used:

OT1:
TCG ACG AGA GCC ATG AAG GTC CTC ATC CTT GCC TGT CTG GTG GCT CTG GCC ATT GCA AGA GAG CAG GAA GAA CTC AAT GTA GTC GGT A,

OT2:
GAT CTA CCG ACT ACA TTG AGT TCT TCC TGC TCT CTT GCA ATG GCC AGA GCC ACC AGA CAG GCA AGG ATG AGG ACC TTC ATG GCT CTC G,

MSP1:
AATAGATCTGCAGTAACTCCTTCCGTAATTG,

MSP2:
AATTCTCGAGTTAGTGGTGGTGGTGGTGGTGACTGCAGAAATACCATC

MSP8:
TAACTCGAGCGAACCATGAAGGTCCTCATCCTTGCCTGTCTGGTGGCTCTGG
CCATTGCA

Diagram of BC620

```
 26 ATGAAGGTCCTCATAATTGCCTGTCTGGTGGCTCTGGCCATTGCAGCCGTCACTCCCTCCGTCATCGATAAC

1▶ M  K  V  L  I  I  A  C  L  V  A  L  A  I  A  A  V  T  P  S  V  I  D  N
 98 ATCCTGTCCAAGATCGAGAACGAGTACGAGGTGCTGTACCTGAAGCCCCTGGCAGGAGTCTACAGGAGCCT

25▶ I  L  S  K  I  E  N  E  Y  E  V  L  Y  L  K  P  L  A  G  V  Y  R  S  L
169 GAAGAAGCAGCTGGAGAACAACGTGATGACCTTCAACGTGAACGTGAAGGATATCCTGAACAGCAGGTTCAA

48▶ K  K  Q  L  E  N  N  V  M  T  F  N  V  N  V  K  D  I  L  N  S  R  F  N
241 CAAGAGGGAGAACTTCAAGAACGTGCTGGAGAGCGATCTGATCCCCTACAAGGATCTGACCAGCAGCAACTA

72▶ K  R  E  N  F  K  N  V  L  E  S  D  L  I  P  Y  K  D  L  T  S  S  N  Y
                                EcoNI (337)
313 CGTGGTCAAAGATCCCTACAAGTTCCTGAACAAGGAGAAGAGAGATAAGTTCCTGAGCAGTTACAATTACAT
                      ─────────────────▶

96▶ V  V  K  D  P  Y  K  F  L  N  K  E  R  D  K  F  L  S  S  Y  N  Y  I
385 CAAGGATAGCATTGACACCGATATCAACTTCGCCAACGATGTCCTGGGATACTACAAGATCCTGTCCGAGAA

120▶ K  D  S  I  D  T  D  I  N  F  A  N  D  V  L  G  Y  Y  K  I  L  S  E  K
457 GTACAAGAGCGATCTGGATAGCATCAAGAAGTACATCAACGATAAGCAGGGAGAGAACGAGAAGTACCTGCC

144▶ Y  K  S  D  L  D  S  I  K  K  Y  I  N  D  K  Q  G  E  N  E  K  Y  L  P
529 CTTCCTGAACAACATCGAGACCCTGTACAAGACCGTCAACGATAAGATTGATCTGTTCGTGATCCACCTGGA

168▶ F  L  N  N  I  E  T  L  Y  K  T  V  N  D  K  I  D  L  F  V  I  H  L  E
                    NdeI (621)
601 GGCCAAGGTCCTGCAGTACACATATGAGAAGAGCAACGTGGAGGTCAAGATCAAGGAGCTGAATTACCTGAA
               ◀─────────────

192▶ A  K  V  L  Q  Y  T  Y  E  K  S  N  V  E  V  K  I  K  E  L  N  Y  L  K
673 GACCATCCAGGATAAGCTGGCCGATTTCAAGAAGAACAACAACTTCGTCGGAATCGCCGATCTGAGCACCGA

216▶ T  I  Q  D  K  L  A  D  F  K  K  N  N  N  F  V  G  I  A  D  L  S  T  D
745 TTACAACCACAACAACCTGCTGACCAAGTTCCTGAGCACCGGAATGGTCTTCGAAAACCTGGCCAAGACCGT

240▶ Y  N  H  N  N  L  L  T  K  F  L  S  T  G  M  V  F  E  N  L  A  K  T  V
                                   BsmI (849)
817 CCTGAGCAACCTGCTGGATGGAAACCTGCAGGGAATGCTGCAGATCAGCCAGCACCAGTGTGTGAAGAAGC
                          ─────────────────▶

264▶ L  S  N  L  L  D  G  N  L  Q  G  M  L  Q  I  S  Q  H  Q  C  V  K  K
888 AGTGTCCCCAGAACAGCGGATGCTTCAGACACCTGGATGAGAGGGAGGAGTGCAAGTGCCTGCTGAACTA

288▶ Q  C  P  Q  N  S  G  C  F  R  H  L  D  E  R  E  E  C  K  C  L  L  N  Y
958 CAAGCAGGAAGGAGATAAGTGTGTGGAAAACCCCAATCCTACTTGTAACGAGAACAATGGAGGATGCGATG

311▶ K  Q  E  G  D  K  C  V  E  N  P  N  P  T  C  N  E  N  N  G  G  C  D
1029 CCGATGCCAAGTGTACCGAGGAGGATTCAGGAAGCAACGGAAAGAAGATCACCTGCGAGTGTACCAAGCCT

335▶ A  D  A  K  C  T  E  E  D  S  G  S  N  G  K  K  I  T  C  E  C  T  K  P
                                                          XhoI (1157)
1100 GATTCTTATCCACTGTTCGATGGtATtTTCTGCAGTCACCACCACCACCACCACTAACTCGAGGAT
                                                                  ◀──────

MODIFIED MSP-1 NUCLEIC ACID SEQUENCES AND METHODS FOR INCREASING MRNA LEVELS AND PROTEIN EXPRESSION IN CELL SYSTEMS

This application claims the benefit of a previously filed Provisional Application No. 60/085,649, filed May 15, 1998, and Provisional Application No. 60/062,592, filed Oct. 20, 1997, the contents of which are incorporated in their entirety.

BACKGROUND OF THE INVENTION

1. Field of the Invention

The invention relates to heterologous gene expression. More particularly, the invention relates to the expression of malaria genes in higher eukaryote cell systems.

2. Summary of the Related Art

Recombinant production of certain heterologous gene products is often difficult in ill vitro cell culture systems or ill vivo recombinant production systems. For example, many researchers have found it difficult to express proteins derived from bacteria, parasites and virus in cell culture systems different from the cell from which the protein was originally derived, and particularly in mammalian cell culture systems. One example of a therapeutically important protein which has been difficult to produce by mammalian cells is the malaria merozoite surface protein (MSP-1).

Malaria is a serious heath problem in tropical countries. Resistance to existing drugs is fast developing and a vaccine is urgently needed. Of the number of antigens that get expressed during the life cycle of *P. falciparum,* MSP-1 is the most extensively studied and promises to be the most successful candidate for vaccination. Individuals exposed to *P. falciparum* develop antibodies against MSP-1, and studies have shown that there is a correlation between a naturally acquired immune response to NISP-1 and reduced malaria morbidity. In a number of studies, immunization with purified native MSP-1 or recombinant fragments of the protein has induced at least partial protection from the parasite (Diggs et al, (1993) *Parasitol Today* 9:300–302). Thus MSP-1 is an important target for the development of a vaccine against *P. falciparum.*

MSP-1 is a 190–220 kDA glycoprotein. The C-terminal region has been the focus of recombinant production for use as a vaccine. However, a major problem in developing MSP-1 as a vaccine is the difficulty in obtaining recombinant proteins in bacterial or yeast expression systems that are equivalent in immunological potency to the affinity purified native protein (Chang et al., (1992) *J. Immunol.* 148:548–555.) and in large enough quantities to make vaccine production feasible.

Improved procedures for enhancing expression of sufficient quantities of MSP-1 would be advantageous.

BRIEF SUMMARY OF THE INVENTION

The present invention provides improved recombinant DNA compositions and procedures for increasing the mRNA levels and protein expression of the malarial surface antigen MSP-1 in cell culture systems, mammalian cell culture systems, or in transgenic mammals. The preferred protein candidate for expression in an expression system in accordance with the invention is a C-terminal derivative of MSP-1 having a DNA coding sequence with reduced AT content, and eliminated mRNA instability motifs and rare codons relative to the recombinant expression systems. Thus, in a first aspect, the invention provides a DNA sequence derived from the sequence shown in SEQ ID NO 2. This derivative sequence is shown in SEQ ID NO 1.

In a second aspect, the invention provides a process for preparing a modified nucleic acid of the invention comprising the steps of lowering the overall AT content of the natural gene encoding MSP-1, eliminating all mRNA instability motifs and replacing all rare codons with a preferred codon of the mammary gland tissue, all by replacing specific codons in the natural gene with codons recognizable to, and preferably preferred by mammary gland tissue and which code for the same amino acids as the replaced codon. This aspect of the invention further includes modified nucleic acids prepared according to the process of the invention.

In a third aspect, the invention also provides vectors comprising modified MSP-1 nucleic acids of the invention and a goat beta casein promoter and signal sequence, and host cells transformed with nucleic acids of the invention.

In a fourth aspect, the invention provides transgenic non-human mammals whose germlines comprise a nucleic acid of the invention.

In a fifth aspect, the invention provides a DNA vaccine comprising a modified MSP-1 gene according to the invention.

DESCRIPTION OF THE DRAWINGS

FIG. 1 depicts the cDNA sequence of MSP-1$_{42}$ modified in accordance with the invention [SEQ ID NO.: 1] in which 306 nucleotide positions have been replaced to lower AT content and eliminate mRNA instability motifs while maintaining the same protein amino acid sequence of MSP-1$_{42}$ [SEQ ID NO. 9]. The large letters indicate nucleotide substitutions.

FIG. 3(A–B) is a codon usage table for wild type MSP-1$_{42}$ (designated "MSP wt" in the table) and the new modified MSP-1$_{42}$ gene (designated "edited MSP" in the table) and several milk protein genes (casein genes derived from goats and mouse). The numbers in each column indicate the actual number of times a specific codon appears in each of the listed genes. The new MSP-1$_{42}$ synthetic gene was derived from the mammary specific codon usage by first choosing GC rich codons for a given amino acid combined with selecting the amino acids used most frequently in the milk proteins.

FIG. 11 is a schematic representation of the nucleotide sequence of MSP42-2 [SEQ ID NO.: 8] and its deduced amino acid sequence [SEQ ID NO.: 11].

DETAILED DESCRIPTION OF THE PREFERRED EMBODIMENTS

The patent and scientific literature referred to herein establishes the knowledge that is available to those with skill in the art. The issued US patents, allowed applications, published foreign applications, and references cited herein are hereby incorporated by reference. Any conflicts between these references and the present disclosure shall be resolved in favor of the present disclosure.

The present invention provides improved recombinant DNA compositions and procedures for increasing the mRNA levels and protein expression of the malarial surface antigen MSP-1 in cell culture systems, mammalian cell culture systems, or in transgenic mammals. The preferred protein candidate for expression in an expression system in accordance with the invention is a C-terminal derivative of MSP-1 having a DNA coding sequence with reduced AT content, and eliminated mRNA instability motifs and rare codons relative to the recombinant expression systems. Thus, in a first aspect, the invention provides a DNA sequence derived from the sequence shown in SEQ ID NO 2. This derivative sequence is shown in SEQ ID NO 1.

In preferred embodiments, the nucleic acid of the invention is capable of expressing MSP-1 in mammalian cell culture systems, or in transgenic mammals at a level which is at least 25%, and preferably 50% and even more preferably at least 100% or more of that expressed by the natural gene in mammalian cell culture systems, or in transgenic mammals under identical conditions.

As used herein, the term "expression" is meant mRNA transcription resulting in protein expression. Expression may be measured by a number of techniques known in the art including using an antibody specific for the protein of interest. By "natural gene" or "native gene" is meant the gene sequence, or fragments thereof (including naturally occurring allelic variations), which encode the wild type form of MSP-1 and from which the modified nucleic acid is derived. A "preferred codon "means a codon which is used more prevalently by the cell or tissue type in which the modified MSP-1 gene is to be expressed, for example, in mammary tissue. Not all codon chances described herein are changes to a preferred codon, so long as the codon replacement is a codon which is at least recognized by the mouse mammary tissue. The term "reduced AT content" as used herein means having a lower overall percentage of nucleotides having A (adenine) or T (thymine) bases relative to the natural MSP-1 gene due to replacement of the A or T containing nucleotide positions or A and/or T containing codons with nucleotides or codons recognized by mouse mammary tissue and which do not change the amino acid sequence of the target protein.

In a second aspect, the invention provides a process for preparing a modified nucleic acid of the invention comprising the steps of lowering the overall AT content of the natural gene encoding MSP-1, eliminating all mRNA instability motifs and replacing all rare codons with a preferred codon of mammary gland tissue, all by replacing specific codons in the natural gene with codons recognizable to, and preferably preferred by mammary gland tissue and which code for the same amino acids as the replaced codon. Standard reference works describing the general principals of recombinant DNA technology include Watson, J. D. et al, *Molecular Biology of the Gene,* Volumes I and II the Benjamin/Cummings Publishing Company, Inc. publisher, Menlo Park, Calif. (1987) Darnell, J. E. et al., *Molecular Cell Biology,* Scientific American Books, Inc., Publisher, New York, N.Y. (1986); Old, R. W., et al., *Principles of Gene Manipulation: An Introduction to Genetic Engineering,* 2d edition, University of California Press, publisher, Berkeley Calif. (1981); Maniatis, T., et al., *Molecular Cloning: A Laboratory, Manual,* $2^{nd}$ ed. Cold Spring Harbor Laboratory, publisher, Cold Spring Harbor, N.Y. (1989) and *Current Protocols in Molecular Biology,* Ausubel et al., Wiley Press, New York, N.Y. (1992). This aspect of the invention further includes modified nucleic acids prepared according to the process of the invention.

Without being limited to any theory, previous research has indicated that a conserved AU sequence (AUUUA) from the 3' untranslated region of GM-CSF mRNA mediates selective mRNA degradation (Shaw, G. and Kamen, R. *Cell* 46:659–667). The focus in the past has been on the presence of these instability motifs in the untranslated region of a gene. The instant invention is the first to recognize an advantage to eliminating the instability sequences in the coding region of the MSP-1 gene.

In a third aspect, the invention also provides vectors comprising modified MSP-1 nucleic acids of the invention and a goat beta casein promoter and signal sequence, and host cells transformed with nucleic acids of the invention.

In a fourth aspect, the invention provides transgenic non-human mammals whose germlines comprise a nucleic acid of the invention. General principals for producing transgenic animals are known in the art. See for example Hogan et al., *Manipulating the Mouse Embryo: A Laboratory Manual,* Cold Spring Harbor Laboratory, (1986); Simons et al, *Bio/Technology* 6:179–183, (1988); Wall et al., *Biol. Reprod.* 32:645–651, (1985); Buhler et al., *Bio/Technology,* 8:140–143 (1990); Ebert et al., *Bio/Technology* 9:835–838 (1991); Krimenfort et al., *Bio/Technology* 9:844–847 (1991); Wall et al., *J. Cell. Biochem.* 49:113–120 (1992). Techniques for introducing foreign DNA sequences into mammals and their germ cells were originally developed in the mouse. See e.g., Gordon et al., *Proc. Natl. Acad. Sci. USA* 77:7380–7384, (1980); Gordon and Ruddle, *Science* 214: 1244–1246 (1981); Palmiter and Brinster, *Cell* 41: 343–345, 1985; Brinster et al., *Proc Natl. Acad Sci., USA* 82:4438–4442 (1985) and Hogan et al. (ibid.). These techniques were subsequently adapted for use with larger animals including cows and goats. Up until very recently, the most widely used procedure for the generation of transgenic mice or livestock, several hundred linear molecules of the DNA of interest in the form of a transgenic expression construct are injected into one of the pro- nuclei of a fertilized egg. Injection of DNA into the cytoplasm of a zygote is also widely used. Most recently cloning of an entire transgenic cell line capable of injection into an unfertilized egg has been achieved (KHS Campbell et al., *Nature* 380 64–66, (1996)).

The mammary gland expression system has the advantages of high expression levels, low cost, correct processing and accessibility. Known proteins, such as bovine and human alpha-lactalbumin have been produced in lactating transgenic animals by several researchers. (Wright et al, *Bio/Technology* 9:830–834 (1991); Vilotte et al, *Eur. J. Biochem.*, 186:43–48 (1989); Hochi et at., *Mol Reprod. And Devel.* 33:160–164 (1992); Soulier et al., *FEBS Letters* 297(1,2):13–18 (1992)) and the system has been shown to produce high levels of protein.

In a fifth aspect, the invention provides a DNA vaccine comprising a modified MSP-1 gene according to the invention. Such DNA vaccines may be delivered without encapsulation, or they may be delivered as part of a liposome, or as part of a viral genome. Generally, such vaccines are delivered in an amount sufficient to allow expression of the modified MSP-1 gene and to elicit an antibody response in an animal, including a human, which receives the DNA vaccine. Subsequent deliveries, at least one week after the first delivery, may be used to enhance the antibody response. Preferred delivery routes include introduction via mucosal membranes, as well as parenteral administration.

EXAMPLE

Creation of Novel Modified MSP-1$_{42}$ Gene

Figure 2:
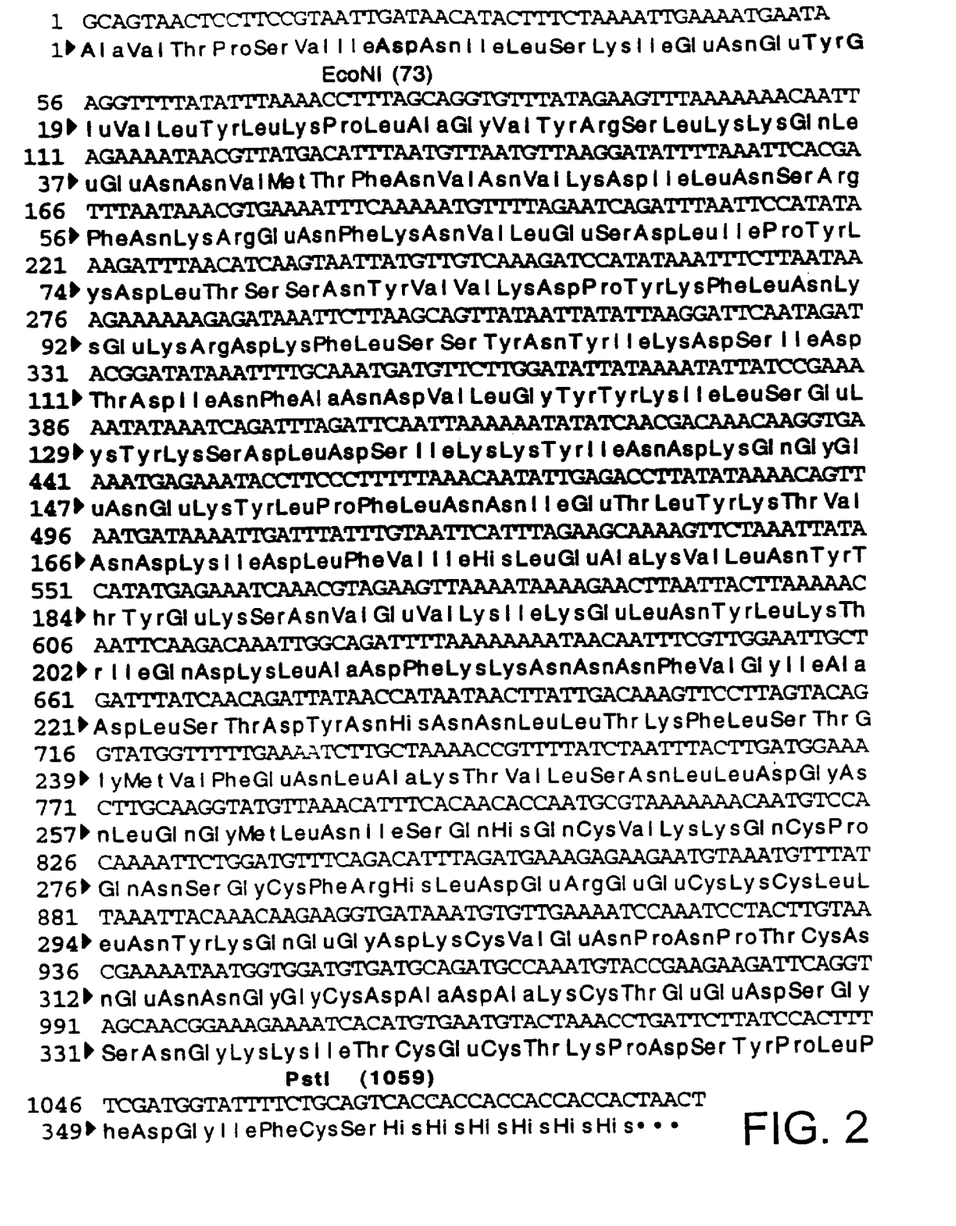
FIG. 2 depicts the nucleotide sequence coding sequence of the "wild type" or native MSP-1$_{42}$ [SEQ ID NO.: 2] and its deduced amino sequence [SEQ ID NO.: 10].

A novel modified nucleic acid encoding the C-terminal fragment of MSP-1 is provided. The novel, modified nucleic acid of the invention encoding a 42 kD C-terminal part of MSP-1 (MSP-1$_{42}$) capable of expression in mammalian cells of the invention is shown in FIG. 1. The natural MSP-1$_{42}$ gene (FIG. 2) was not capable of being expressed in mammalian cell culture or in transgenic mice Analysis of the natural MSP-1$_{42}$ gene suggested several characteristics that distinguish it from mammalian genes. First, it has a very high overall AT content of 76%. Second, the mRNA instability motif, AUUUA, occurred 10 times in this 1100 bp DNA segment (FIG. 2). To address these differences a new MSP-1$_{42}$ gene was designed. Silent nucleotide substitution was introduced into the native MSP-1$_{42}$ gene at 306 positions to reduce the overall AT content to 49.7%. Each of the 10 AUUUA mRNA instability motifs in the natural gene were eliminated by changes in codon usage as well. To change the codon usage, a mammary tissue specific codon usage table, FIG. 3a, was created by using several mouse and goat mammary specific proteins. The table was used to guide the choice of codon usage for the modified M5P-1$_{42}$ gene as described above. For example as shown in the Table in FIG. 3a, in the natural gene, 65% (25/38) of the Leu was encoded by TTA, a rare codon in the mammary gland. In the modified MSP-1$_{42}$ gene, 100% of the Leu was encoded by CTG, a preferred codon for Leu in the mammary gland.

Figure 4A:
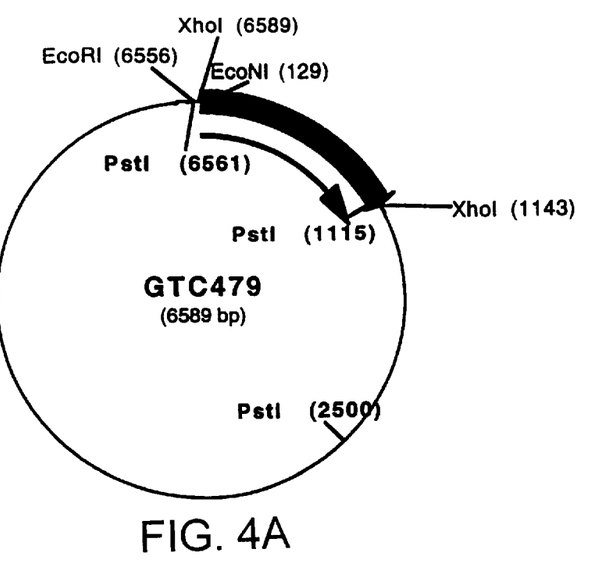
FIG. 4a–c depict MSP-1$_{42}$ constructs GTC 479, GTC 564, and GTC 627, respectively as are described in the examples.
Figure 4B:
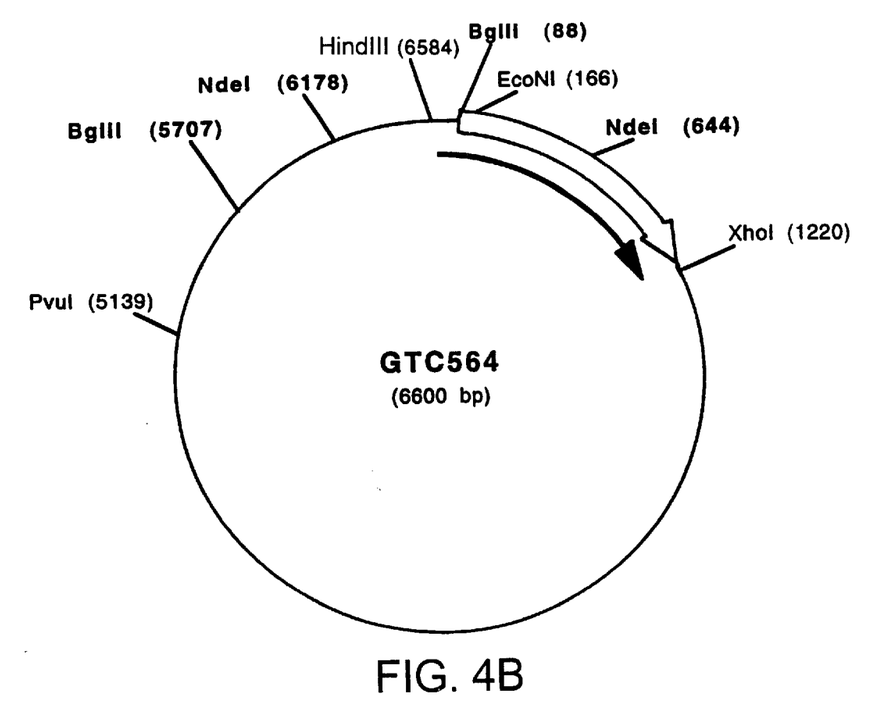
Figure 4C:
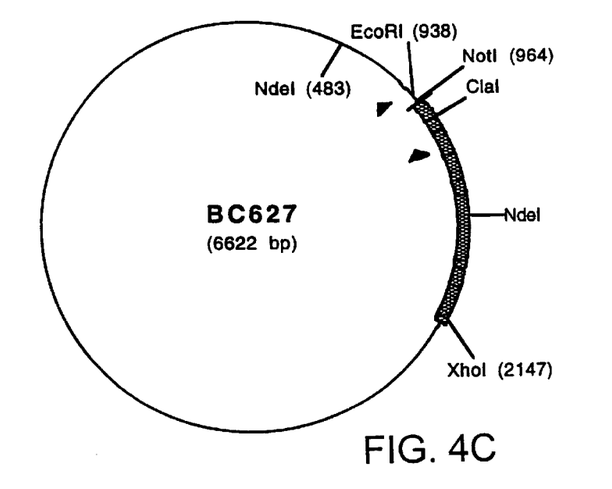

An expression vector was created using the modified MSP-1$_{42}$ gene by fusing the first 26 amino acids of goat beta-casein to the N-terminal of the modified MSP-1$_{42}$ gene and a SalI-Xho I fragment which carries the fusion gene was subcloned into the XhoI site of the expression vector pCDNA3. A His6 tag was fused to the 3' end of the MSP-1$_{42}$ gene to allow the gene product to be affinity purified. This resulted in plasmid GTC627 (FIG. 4c).

To compare the natural MSP-1$_{42}$ gene construct to the modified MSP-1$_{42}$ nucleic acid of the invention, an expression vector was also created for the natural MSP-1$_{42}$ gene and the gene was added to mammalian cell culture and injected into mice to form transgenic mice as follows:

Construction of the Native MSP-1$_{42}$ Expression Vector

Figure 6:
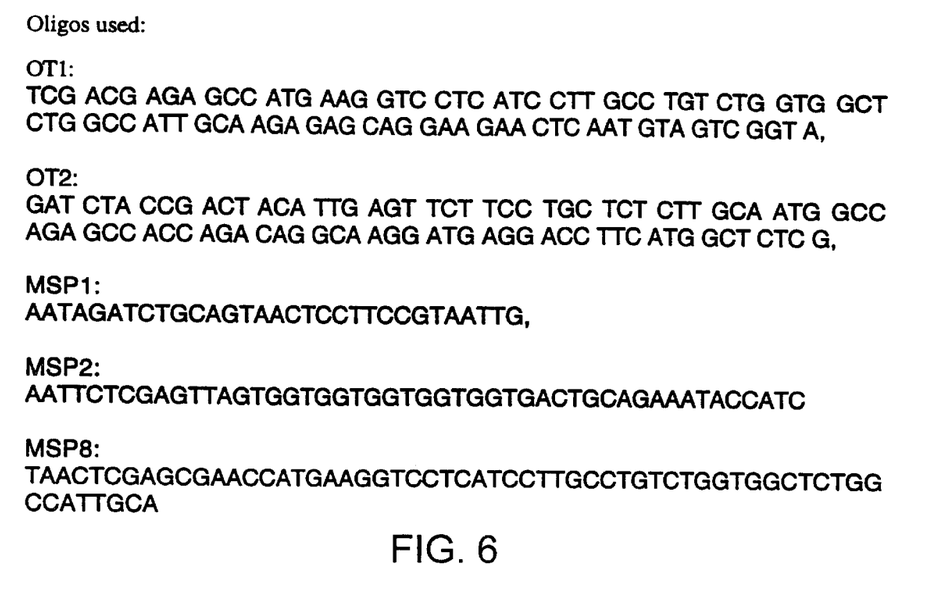
FIG. 6 depicts the nucleic acid sequences of TO1 [SEQ ID NO 3], TO2 [SEQ ID NO 4], MSP-8 [SEQ ID ON 5], MSP-2 [SEQ ID NO 6] and MSP1 [SEQ ID NO 7] described in the Examples.

To secrete the truncated merozoite surface protein-1 (MSP-1) of Plasmodium falciparum, the wild type gene encoding the 42KD C-terminal part of MSP-1 (MSP-1$_{42}$) was fused to either the DNA sequence that encodes the first 15 or the first 26 amino acids of the oat beta-casein. This is achieved by first FCR amplify the MSP-1 plasmid (received from Dr. David Kaslow, NIH) with primers MSP1 and MSP2 (FIG. 6), then cloned the PCR product into the TA vector (Invitrogen). The BgIII-XhoI fragments of the PCR product was ligated with oligos TO1 and TO2 (FIG. 6) into the expression vector pCDNA3. This yielded plasmid GTC564 (FIG. 4b), which encodes the 15 amino acid beta-casein signal peptide and the first 11 amino acids of the mature goat beta-casein followed by the native MSP-1$_{42}$ gene. Oligos MSF-8 and MSP-2 (FIG. 6) were used to amplify MSP-1 plasmid by FCR, the product was then cloned into TA vector. The XhoI fragment was exercised and cloned into the XhoI site of the expression vector pCDNA3 to yield plasmid GTC479 (FIG. 4a), which encoded 15 amino acid goat beta-casein signal peptide fused to the wild-type MSP-1$_{42}$ gene. A His6 tag was added to the 3' end of MSP-1$_{42}$ gene in GTC 564 and CTC 479.

Native MSP-1$_{42}$ Gene is not Expressed in COS-7 Cells

Expression of the native MSP gene in cultured COS-7 cells was assayed by transient transfection assays. GTC479 and GTC564 plasmids DNA were introduced into COS-7 cells by lipofectamine (Gibco-BRL) according to manufacturer's protocols. Total cellular RNA was isolated from the COS cells two days post-transfection. The newly synthesized proteins were metabolically labeled for 10 hours by adding $^{35}$S methionine added to the culture media two days-post transfection.

To determine the MSP mRNA expression In the COS cells, a Northern blot was probed with a $^{32}$p labeled DNA fragment from GTC479. No MSP RNA was detected in GTC479 or GTC564 transfectants (data not shown). Prolong,ed exposure revealed residual levels of degraded MSP mRNA. The $^{35}$S labeled culture supernatants and the lysates were immunoprecipitated with a polyclonal antibody raised against MSP. Immunoprecipitation experiments showed that no expression from either the lysates or the supernatants of the GTC479 or GTC564 transfected cells (data not shown). These results showed that the native MSP-1 gene was not expressed in COS cells.

Figure 7:
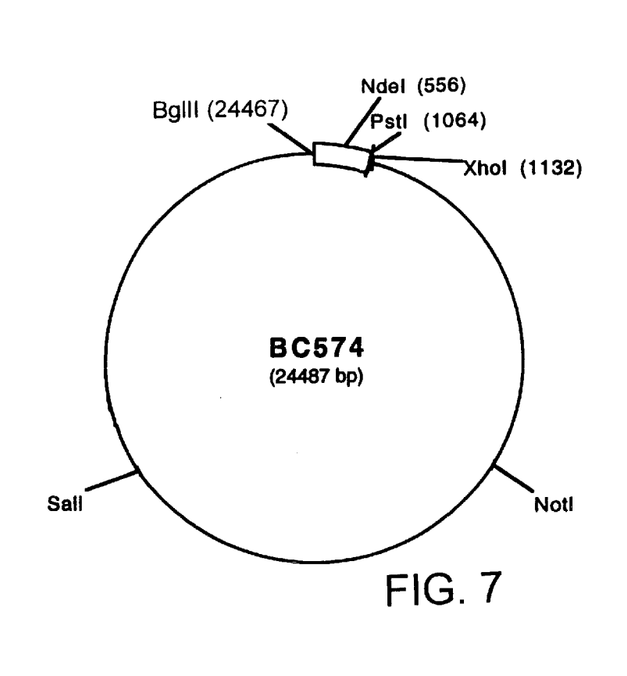
FIG. 7 is a schematic representation of plasmid BC574.
Figure 8:
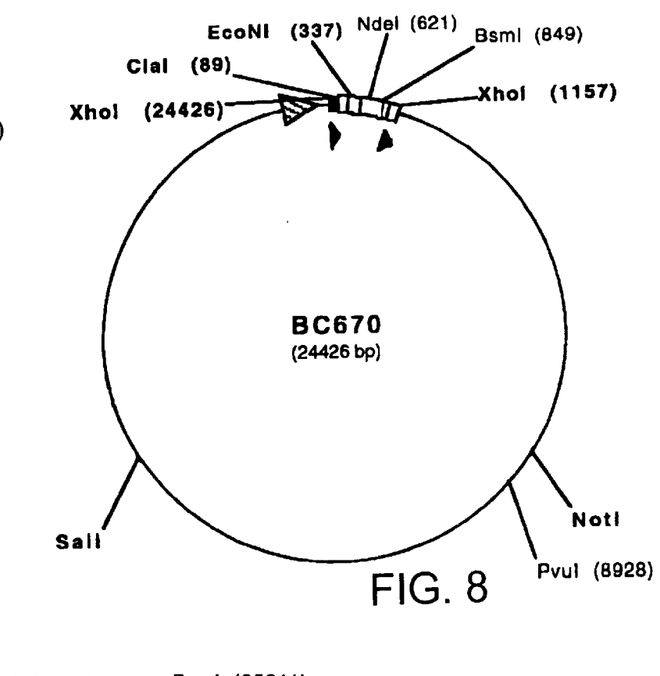
FIG. 8 is a schematic representation of BC620.
Figure 9:
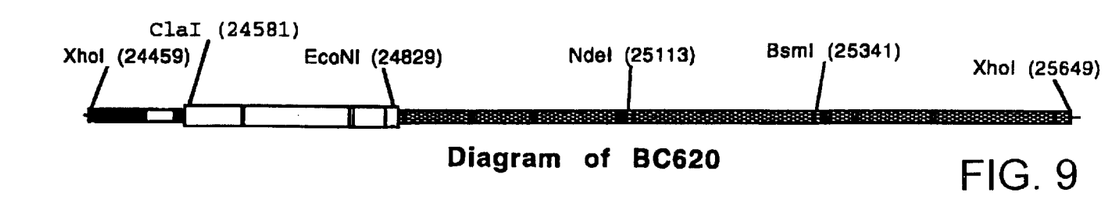
FIG. 9 is a schematic representation of BC670.
Figure 10:
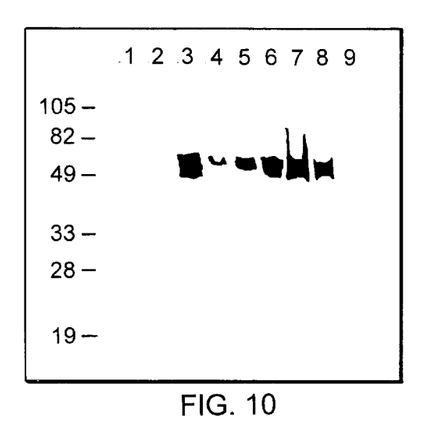
FIG. 10 is a representation of a Western blot of MSP transgenic milk.
Figure 12:
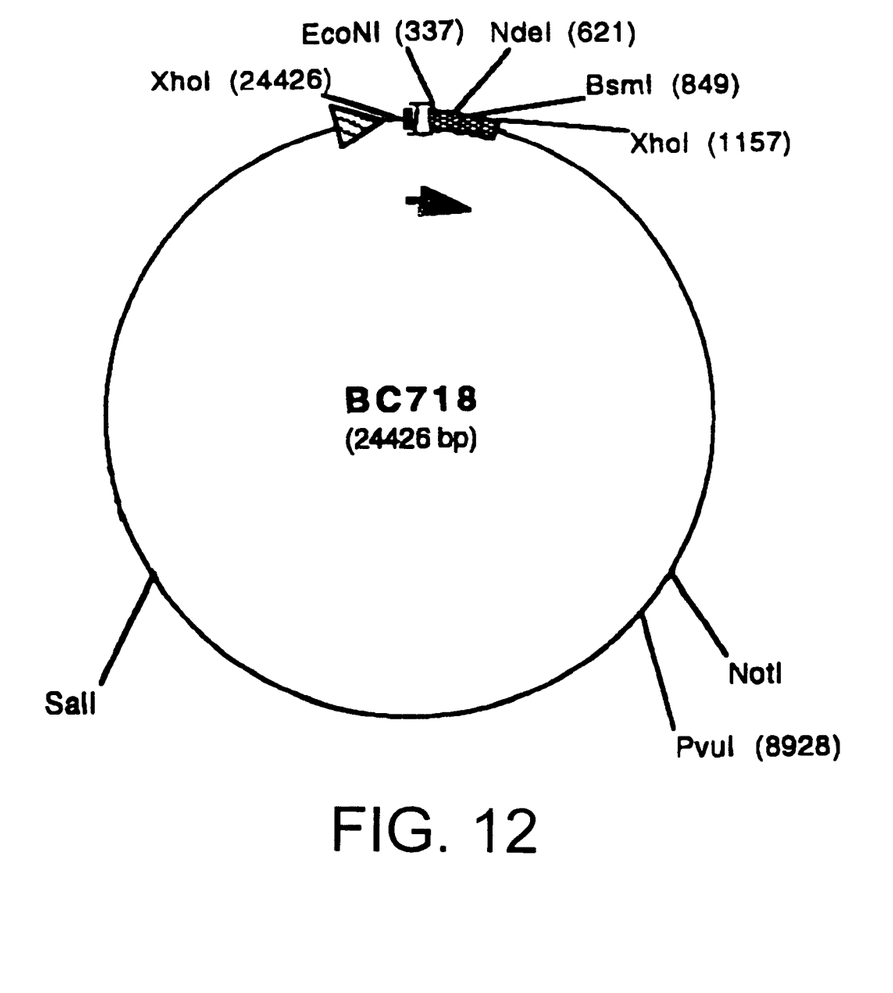
FIG. 12 is a schematic representation of the BC-718.
Figure 13:
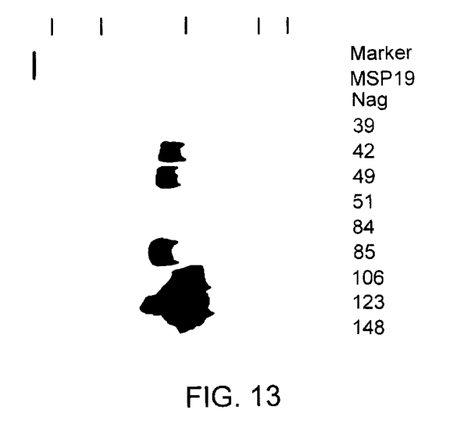
FIG. 13 is a representation of a Western blot of BC-718 expression in transgenic milk.

Native MSP-1$_{42}$ Gene is not Expressed in the Mammary Gland of Transgenic Mice The SalI-Xhot fragment of GTC479, which encoded the 15 amino acids of goat beta-casein signal peptide, the first 11 amino acids of goat beta-casein, and the native MSP-1$_{42}$ gene, was cloned into the XhoI site of the beta-casein expressed in vector BC350. This yielded plasmid BC574 (FIG. 7). A SalI-NotI fragment of BC574 was injected into the mouse embryo to generate transgenic mice. Fifteen lines of transgenic mice were established. Milk from the female founder mice was collected and subjected to Western analysis with polycolonal antibodies against MSP. None of the seven mice analyzed were found to express MSP-1$_{42}$ protein in their milk. To further determine if the mRNA of MSP-1$_{42}$ was expressed in the mammary gland, total RNA was extracted from day 11 lactating transgenic mice and analyzed by Northern blotting. No MSP-1$_{42}$ mRNA was detected by any of the BC 574 lines analyzed. Therefore, the MSP-1$_{42}$ transgene was not expressed in the mammary gland of transgenic mice. Taken together, these experiments suggest that native parasitic MSP-1$_{42}$ gene could not be expressed in mammalian cells, and the block is as the level of mRNA abundance.

Expression of MSP in the Mammalian Cells

Figure 5:
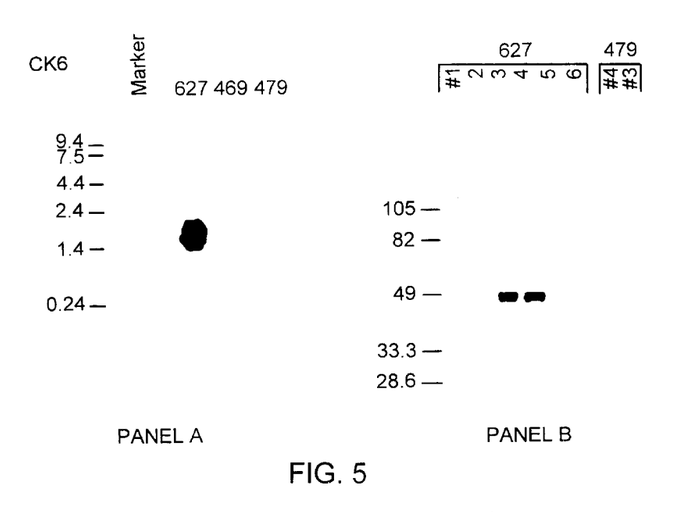
FIG. 5 panel A is a Northern analysis wherein construct GTC627 comprises the new MSP-1$_{42}$ gene modified in accordance with the invention, GTC479 is the construct comprising the native MSP-1$_{42}$ gene, and construct GTC469 is a negative control DNA FIG. 5 panel B is a Western analysis wherein the eluted fractions after affinity purifications numbers are collected fractions. The results show that fractions from GTC679 the modified MSP-1$_{42}$ synthetic gene construct reacted with polyclonal antibodies to MSP-1 and the negative control GTC479 did not.

Transient transfection experiments were performed to evaluate the expression of the modified MSP-1$_{42}$ gene of the invention in COS cells. GTC627 and CTC479 DNA were introduced into the COS-7 cells. Total RNA was isolated 48 hours post-transfection for Northern analysis. The immobilized RNA was probed with $^{32}$P labeled SalI-XhoI fragment of GTC627. A dramatic difference was observed between GTC479 and GTC627. While no MSP-1$_{42}$ mRNA was detected in the GTC479 transfected cells as shown previously, abundant MSP-1$_{42}$ mRNA was expressed by GTC627 (FIG. 5, Panel A). GTC 469 was used as a negative control and comprises the insert of GTC564 cloned into cloning vector PU19, a commercially available cloning vector. A metabolic labeling experiment with $^{35}$S methionine followed by immunoprecipitation with polyclonal antibody (provided by D. Kaslow NIAID, NIH) against MSP showed that MSP-1$_{42}$ protein was synthesized by the transfected COS cells (FIG. 5, Panel B). Furthermore, MSP-1$_{42}$ was detected in the transfected COS supernatant, indicating the MSP-1$_{42}$ protein was also secreted. Additionally, using Ni-NTA column, MSP-1$_{42}$ was affinity purified from the GTC627 transfected COS supernatant.

These results demonstrated that the modification of the parasitic MSP-1$_4$ gene lead to the expression of MSP mRNA in the COS cells. Consequently, the MSP-1$_{42}$ product was synthesized and secreted by mammalian cells.

Polyclonal antibodies used in this experiment may also be prepared by means well known in the art (*Antibodies: A Laboratory Manual*, Ed Harlow and David Lane, eds. Cold Spring Harbor Laboratory, publishers (1988)). Production of MSP serum antibodies is also described in Chang et at., *Infection and Immunity* (1996) 64:253–261 and Chang et al., (1992) *Proc Natl. Acad. Sci. USA* 86:6343–6347.

The results of this analysis indicate that the modified MSP-$1_{42}$ nucleic acid of the invention is expressed at a very high level compared to that of the natural protein which was not expressed at all. These results represent the first experimental evidence that reducing the AT % in a gene leads to expression of the MSP gene in heterologous systems and also the first evidence that removal of AUUUA mRNA instability motifs from the MSP coding region leads to the expression of MSP protein in COS cells. The results shown in FIG. 5, Panel A Northern (i.e. no RNA with native gene and reasonable levels with a modified DNA sequence in accordance with the invention), likely explains the increase in protein production.

The following examples describe the expression of MSP1-42 as a native non-fusion (and non-glycosylated) protein in the milk of transgenic mice.

Construction of MSP Transgene

To fuse MSP1-42 to the 15 amino acid β-casein signal peptide, a pair of oligos, MSP203 and MSP204 (MSP203: [SEQ ID NO.: 12]: ggccgctcgacgccaccatgaaggtcctcataa ttgcctgtctggtggctctggccattgcagccgtcactccctccgtcat, MSP204: [SEQ ID NO.: 13]: cgatgacggagggagtgacgg ctg-caatggccagagccaccagacaggcaattatgaggaccttcatggtggcg tcgagc), which encode the 15 amino acid casein signal and the first 5 amino acids of the MSP1-42 ending at the ClaI site, was ligated with a ClaI-XhoI fragment of BC620 (FIG. 8) which encodes the rest of the MSP1-42 gene, into the XhoI site of the expression vector pCDNA3. A XhoI fragment of this plasmid (GTC669) was then cloned into the XhoI site of milk specific expression vector BC350 to generate B670 (FIG. 9).

Expression of MSP1-42 in the Milk of Transgenic Mice

A SalI-NotI fragment was prepared from plasmid BC670 and microinjected into the mouse embryo to generate transgenic mice. Transgenic mice was identified by extracting mouse DNA from tail biopsy followed by PCR analysis using oligos GTC17 and MSP101 (sequences of oligos: GTC17 [SEQ ID NO.: 14], GATTGACAAGTAATA CGCTGTTTCCTC, Oligo MSP101 [SEQ ID NO. 15], GGATTCAATAGATACGG). Milk from the female founder transgenic mice was collected at day 7 and day 9 of lactation, and subjected to western analysis to determine the expression level of MSP-1-42 using a polyclonal anti-MSP antibody and monoclonal anti MSP antibody 5.2 (Dr. David Kaslow, NIH). Results indicated that the level of MSP-1-42 expression in the milk of transgenic mice was at 1–2 mg/ml (FIG. 10).

Construction of MSP1-42 Glycosylation Sites Minus Mutants

Our analysis of the milk-produced MSP revealed that the transgenic MSP protein was N-glycosylated. To eliminate the N-glycosylation sites in the MSP1-42 gene, Asn (N) at positions 182 and 263 were substituted with Gln (Q). The substitutions were introduced by designing DNA oligos that anneal to the corresponding region of MSP1 and carry the AAC to CAG mutations. These oligos were then used as PCR primers to produce DNA fragments that encode the N to Q substitutions.

To introduce N263-Q mutation, a pair of oligos, MSPGYLYCO-3 [SEQ ID NO.: 16] (CAGGGAATG CTGCAGATCAGC) and MSP42-2 [SEQ ID NO.: 17] (AATTCTCGAGTTAGTGGTGGTGGTGGTGGTGAT CGCAGAAAATACCATG, FIG. 11), were used to PCR amplify plasmid GTC627, which contains the synthetic MSP1-42 gene. The PCR product was cloned into pCR2.1 vector (Invitrogen). This generated plasmid GTC716.

To introduce N182-Q mutation, oligos MSPGLYCO-1 [SEQ ID NO.: 18] (CTCCTTGTTCAGGAACTT GTAGGG) and MSPGLCO-2 (GTCCTGCAGTACACA TATGAG, FIG. 4) were used to amplify plasmid GTC627. The PCR product was cloned into pCR2.1. This generated plasmid GTC700.

The MSP double glycosylation mutant was constructed by the following three steps: first a Xho I-Bsm I 1fragment of BC670 and the Bsm I-Xho I fragment of GTC716 is ligated into the Xho I site of vector pCR2.1. This resulted a plasmid that contain the MSP-1-42 gene with N262-Q mutation. EcoN I-Nde I fragment of this plasmid was then replaced by the EcoN I-Nde I fragment from plasmid GTC716 to introduce the second mutation N181-Q. A Xho I fragment of this plasmid was finally cloned into BC350 to generate BC718 (FIG. 12).

Transgenic Expression Nonglycosylated MSP-1

BC718 has the following characteristics: it carries the MSP1-42 gene under the control of the β-casein promoter so it can be expressed in the mammary gland of the transgenic animal during lactation. Further, it encodes a 15 amino acid β-casein leader sequence fused directly to MSP1-42 so that the MSP1-42, without any additional amino acid at its N-terminal, can be secreted into the milk. Finally, because the N-Q substitutions, the MSP produced in the milk of the transgenic animal by this construct will not be N-glycosylated. Taken together, the transgenic MSP produced in the milk by BC718 is the same as the parasitic MSP.

A SalI/XhoI fragment was prepared from plasmid BC718 and microinjected into mouse embryos to generate transgenic mice. Transgenic animals were identified as described previously. Milk from female founders was collected and analyzed by Western blotting with antibody 5.2. The results, shown in FIG. 13 indicate expression of nonglycosylated MSP1 at a concentration of 0.5 to 1 mg/ml.

SEQUENCE LISTING

<160> NUMBER OF SEQ ID NOS: 8

<210> SEQ ID NO 1
<211> LENGTH: 1065
<212> TYPE: DNA
<213> ORGANISM: preferably, a bacterium, virus, or parasite

<400> SEQUENCE: 1

| | | | | | |
|---|---|---|---|---|---|
| gccgtcactc | cctccgtcat | cgataacatc | ctgtccaaga | tcgagaacga | gtacgaggtg | 60 |
| ctgtacctga | agccgctggc | agggtctac | cggagcctga | agaagcagct | ggagaacaac | 120 |
| gtgatgacct | tcaacgtgaa | cgtgaaggat | atcctgaaca | gccggttcaa | caagcgggag | 180 |
| aacttcaaga | acgtgctgga | gagcgatctg | atcccctaca | aggatctgac | cagcagcaac | 240 |
| tacgtggtca | aggatcccta | caagttcctg | aacaaggaga | agagagataa | gttcctgagc | 300 |
| agttacaact | acatcaagga | tagcattgat | accgatatca | acttcgccaa | cgatgtcctg | 360 |
| ggatactaca | agatcctgtc | cgagaagtac | aagagcgatc | tggattcaat | caagaagtac | 420 |
| atcaacgata | agcagggaga | gaacgagaag | tacctgccct | tcctgaacaa | catcgagacc | 480 |
| ctgtacaaga | ccgtcaacga | taagattgat | ctgttcgtga | tccacctgga | ggccaaggtc | 540 |
| ctgaactaca | catatgagaa | gagcaacgtg | gaggtcaaga | tcaaggagct | gaattacctg | 600 |
| aagaccatcc | aggataagct | ggccgatttc | aagaagaaca | caacttcgt | cgggatcgcc | 660 |
| gatctgagca | ccgattacaa | ccacaacaac | ctgctgacca | gttcctgag | caccggtatg | 720 |
| gtcttcgaaa | acctggccaa | gaccgtcctg | agcaacctgc | tggatgggaa | cctgcagggg | 780 |
| atgctgaaca | tcagccagca | ccagtgtgtg | aagaagcagt | gtccccagaa | cagcgggtgt | 840 |
| ttcagacacc | tggatgagag | agaggagtgt | aagtgtctgc | tgaactacaa | gcaggaaggt | 900 |
| gataagtgtg | tggaaaaccc | caatcctact | tgtaacgaga | caatggtgg | atgtgatgcc | 960 |
| gatgccaagt | gtaccgagga | ggattcaggg | agcaacggga | agaagatcac | ctgtgagtgt | 1020 |
| accaagcctg | attcttatcc | actgttcgat | ggtatcttct | gtagt | | 1065 |

<210> SEQ ID NO 2
<211> LENGTH: 1088
<212> TYPE: DNA
<213> ORGANISM: preferably, a bacterium, virus, or parasite

<400> SEQUENCE: 2

| | | | | | |
|---|---|---|---|---|---|
| gcagtaactc | cttccgtaat | tgataacata | ctttctaaaa | ttgaaatga | atatgaggtt | 60 |
| ttatatttaa | aacctttagc | aggtgtttat | agaagtttaa | aaaaacaatt | agaaaataac | 120 |
| gttatgacat | ttaatgttaa | tgttaaggat | atttttaaatt | cacgatttaa | taaacgtgaa | 180 |
| aatttcaaaa | atgttttaga | atcagattta | attccatata | aagatttaac | atcaagtaat | 240 |
| tatgttgtca | aagatccata | taaatttctt | aataaagaaa | aagagataa | attcttaagc | 300 |
| agttataatt | atattaagga | ttcaatagat | acggatataa | attttgcaaa | tgatgttctt | 360 |
| ggatattata | aaatattatc | cgaaaaatat | aaatcagatt | tagattcaat | taaaaaatat | 420 |
| atcaacgaca | aacaaggtga | aaatgagaaa | taccttccct | ttttaaacaa | tattgagacc | 480 |
| ttatataaaa | cagttaatga | taaaattgat | ttatttgtaa | ttcatttaga | agcaaaagtt | 540 |
| ctaaattata | catatgagaa | atcaaacgta | gaagttaaaa | taaagaact | taattactta | 600 |
| aaaacaattc | aagacaaatt | ggcagatttt | aaaaaaaata | caatttcgt | tggaattgct | 660 |
| gatttatcaa | cagattataa | ccataataac | ttattgacaa | agttccttag | tacaggtatg | 720 |

```
gtttttgaaa atcttgctaa aaccgtttta tctaatttac ttgatggaaa cttgcaaggt    780
atgttaaaca tttcacaaca ccaatgcgta aaaaaacaat gtccacaaaa ttctggatgt    840
ttcagacatt tagatgaaag agaagaatgt aaatgtttat taaattacaa acaagaaggt    900
gataaatgtg ttgaaaatcc aaatcctact tgtaacgaaa ataatggtgg atgtgatgca    960
gatgccaaat gtaccgaaga agattcaggt agcaacggaa agaaaatcac atgtgaatgt   1020
actaaacctg attcttatcc acttttcgat ggtatttttct gcagtcacca ccaccaccac   1080
cactaact                                                             1088

<210> SEQ ID NO 3
<211> LENGTH: 88
<212> TYPE: DNA
<213> ORGANISM: preferably, a bacterium, virus, or parasite

<400> SEQUENCE: 3
tcgacgagag ccatgaaggt cctcatcctt gcctgtctgg tggctctggc cattgcaaga     60
gagcaggaag aactcaatgt agtcggta                                        88

<210> SEQ ID NO 4
<211> LENGTH: 88
<212> TYPE: DNA
<213> ORGANISM: preferably, a bacterium, virus, or parasite

<400> SEQUENCE: 4
gatctaccga ctacattgag ttcttcctgc tctcttgcaa tggccagagc caccagacag     60
gcaaggatga ggaccttcat ggctctcg                                        88

<210> SEQ ID NO 5
<211> LENGTH: 60
<212> TYPE: DNA
<213> ORGANISM: preferably, a bacterium, virus, or parasite

<400> SEQUENCE: 5
taactcgagc gaaccatgaa ggtcctcatc cttgcctgtc tggtggctct ggccattgca     60

<210> SEQ ID NO 6
<211> LENGTH: 48
<212> TYPE: DNA
<213> ORGANISM: preferably, a bacterium, virus, or parasite

<400> SEQUENCE: 6
aattctcgag ttagtggtgg tggtggtggt gactgcagaa ataccatc                  48

<210> SEQ ID NO 7
<211> LENGTH: 31
<212> TYPE: DNA
<213> ORGANISM: preferably, a bacterium, virus, or parasite

<400> SEQUENCE: 7
aatagatctg cagtaactcc ttccgtaatt g                                    31

<210> SEQ ID NO 8
<211> LENGTH: 1142
<212> TYPE: DNA
<213> ORGANISM: preferably, a bacterium, virus, or parasite

<400> SEQUENCE: 8
atgaaggtcc tcataattgc ctgtctggtg gctctggcca ttgcagccgt cactccctcc     60
```

-continued

```
gtcatcgata acatcctgtc caagatcgag aacgagtacg aggtgctgta cctgaagccc      120
ctggcaggag tctacaggag cctgaagaag cagctggaga acaacgtgat gaccttcaac      180
gtgaacgtga aggatatcct gaacagcagg ttcaacaaga gggagaactt caagaacgtg      240
ctggagagcg atctgatccc ctacaaggat ctgaccagca gcaactacgt ggtcaaagat      300
ccctacaagt tcctgaacaa ggagaagaga gataagttcc tgagcagtta caattacatc      360
aaggatagca ttgacaccga tatcaacttc gccaacgatg tcctgggata ctacaagatc      420
ctgtccgaga agtacaagag cgatctggat agcatcaaga agtacatcaa cgataagcag      480
ggagagaacg agaagtacct gcccttcctg aacaacatcg agaccctgta caagaccgtc      540
aacgataaga ttgatctgtt cgtgatccac ctggaggcca aggtcctgca gtacacatat      600
gagaagagca acgtggaggt caagatcaag gagctgaatt acctgaagac catccaggat      660
aagctggccg atttcaagaa gaacaacaac ttcgtcggaa tcgccgatct gagcaccgat      720
tacaaccaca acaacctgct gaccaagttc ctgagcaccg gaatggtctt cgaaaacctg      780
gccaagaccg tcctgagcaa cctgctggat ggaaacctgc agggaatgct gcagatcagc      840
cagcaccagt gtgtgaagaa gcagtgtccc cagaacagcg gatgcttcag acacctggat      900
gagagggagg agtgcaagtg cctgctgaac tacaagcagg aaggagataa gtgtgtggaa      960
aaccccaatc ctacttgtaa cgagaacaat ggaggatgcg atgccgatgc caagtgtacc     1020
gaggaggatt caggaagcaa cggaaagaag atcacctgcg agtgtaccaa gcctgattct     1080
tatccactgt tcgatggtat tttctgcagt caccaccacc accaccacta actcgaggat     1140
cc                                                                    1142
```

What is claimed is:

1. A modified nucleic acid sequence comprising SEQ ID NO 1.

2. A nucleic acid sequence comprising a modified nucleic acid sequence encoding a merozoite surface protein 1 (MSP-1) operably linked to a promoter which directs expression in mammary epithelial cells wherein the AT content of the modified nucleic acid sequence has been reduced by replacing codons from a nucleic acid sequence of SEQ ID NO:2 with mammary gland preferred codons encoding the same amino acid as the replaced codon such that the AT content of the modified nucleic acid sequence is 50% or less.

3. A vector comprising a modified merozoite surface protein 1 (MSP-1) nucleic acid according to clam 2.

4. The vector of claim 3, wherein the promoter is a beta casein promoter.

5. A host cell transformed with the vector according to claim 3.

6. The cell of claim 5, wherein the cell is a mammalian cell.

7. The cell of claim 6, wherein the cell is a COS cell.

8. The cell of claim 6, wherein the cell is a mammary gland epithelial cell.

9. The nucleic acid of claim 2, wherein the modified nucleic acid comprises at least one additional mammary gland preferred codon other than the mammary gland preferred codons which lowers the AT content.

10. A nucleic acid sequence comprising a modified nucleic acid sequence encoding a merozoite surface protein 1 (MSP-1) operably linked to a promoter which directs expression in mammary epithelial cells wherein the AT content of the modified nucleic acid sequence has been reduced by replacing codons from a nucleic acid sequence of SEQ ID NO:2 with mammary gland preferred codons such that the AT content of the modified nucleic acid sequence is 50% or less and, wherein at least one glycosylation site of SEQ ID NO:10 has been altered such that it is not functional.

11. The nucleic acid of claim 10, wherein the glycosylation site which is not functional is at position 182 of SEQ ID NO:10.

12. The nucleic acid of claim 10, wherein the glycosylation site which is not functional is at position 263 of SEQ ID NO:10.

13. The nucleic acid of claim 9, wherein the promoter is a beta casein promoter.

14. The nucleic acid of claim 10, wherein the promoter is a beta casein promoter.

15. A nucleic acid comprising a modified nucleic acid encoding merozoite surface protein 1 (MSP-1) operably linked to a promoter which directs expression in mammary epithelial cells, wherein all mRNA instability motifs present in the wild-type nucleic acid sequence encoding MSP-1 have been eliminated by replacing codons of SEQ ID NO:2 with mammary gland preferred codons encoding the same amino acid as the replaced codon.

16. The nucleic acid of claim 15, wherein the promoter is a beta casein promoter.

17. The nucleic acid of claim 15, wherein the modified nucleic acid comprises at least one additional mammary gland preferred codon other than the codon replaced to eliminate an mRNA instability motif.

18. The nucleic acid of claim 15, wherein all of the codons of the modified nucleic acid are mammary gland preferred codons.

19. A nucleic acid comprising a modified nucleic acid encoding merozoite surface protein 1 (MSP-1) operably linked to a promoter which directs expression in mammary epithelial cells, wherein all mRNA instability motifs present in the wild-type nucleic acid sequence encoding MSP-1 have been eliminated by replacing codons of SEQ ID NO:2 with mammary gland preferred codons, and wherein at least one glycosylation site of SEQ ID NO:10 has been altered such that it is not functional.

20. The nucleic acid of claim 19, wherein the glycosylation site which is not functional is at position 182 of SEQ ID NO:10.

21. The nucleic acid of claim 19, wherein the glucosylation site which is not functional is at position 263 of SEQ ID NO:10.

22. The nucleic acid of claim 19, wherein the glycosylation sites at positions 182 and 263 of SEQ ID NO:10 are not functional.

* * * * *